US009668779B2

(12) United States Patent
Okamoto

(10) Patent No.: US 9,668,779 B2
(45) Date of Patent: Jun. 6, 2017

(54) TRANSVERSE VERTEBRAL CONNECTOR

(71) Applicant: Phygen, LLC, Irvine, CA (US)

(72) Inventor: Bryan Okamoto, Irvine, CA (US)

(73) Assignee: PHYGEN, LLC, Irvine, CA (US)

( * ) Notice: Subject to any disclaimer, the term of this patent is extended or adjusted under 35 U.S.C. 154(b) by 0 days.

(21) Appl. No.: 14/071,463

(22) Filed: Nov. 4, 2013

(65) Prior Publication Data
US 2014/0128919 A1    May 8, 2014

Related U.S. Application Data

(60) Provisional application No. 61/722,461, filed on Nov. 5, 2012.

(51) Int. Cl.
*A61B 17/70* (2006.01)
(52) U.S. Cl.
CPC ................. *A61B 17/7052* (2013.01)
(58) Field of Classification Search
CPC ..... A61B 17/68; A61B 17/70; A61B 17/7004; A61B 17/7019; A61B 17/7043; A61B 17/7049; A61B 17/705; A61B 17/75; A61B 2017/7073; A61B 17/7052
USPC .... 606/250–253, 276–279, 53, 60, 246, 324
See application file for complete search history.

(56) References Cited

U.S. PATENT DOCUMENTS

| | | | |
|---|---|---|---|
| 6,074,391 A * | 6/2000 | Metz-Stavenhagen et al. | 606/278 |
| 6,321,625 B1 * | 11/2001 | Fernandez | 81/176.2 |
| 8,361,117 B2 * | 1/2013 | Michielli et al. | 606/253 |
| 8,372,120 B2 * | 2/2013 | James | 606/250 |
| 2004/0133203 A1 * | 7/2004 | Young et al. | 606/61 |
| 2011/0282388 A1 * | 11/2011 | Young et al. | 606/252 |
| 2013/0053888 A1 * | 2/2013 | Torres | 606/252 |

* cited by examiner

*Primary Examiner* — Ellen C Hammond
*Assistant Examiner* — Tessa Matthews
(74) *Attorney, Agent, or Firm* — Wilson, Sonsini, Goodrich & Rosati

(57) ABSTRACT

Devices are adapted for interconnecting first and second longitudinal members extending along a spinal column of a patient. The devices are particularly suited for use in the cervical region of the spine.

6 Claims, 5 Drawing Sheets

TRANSVERSE VERTEBRAL CONNECTOR

REFERENCE TO RELATED APPLICATIONS

This application claims priority benefit under 35 U.S.C. §119(e) of U.S. Provisional Patent Application Ser. No. 61/722,461, filed Nov. 5, 2012 and entitled "TRANSVERSE VERTEBRAL CONNECTOR." Priority to the filing date is hereby claimed and the disclosure of the patent application is hereby incorporated by reference in its entirety.

BACKGROUND

The use of spinal rods is conventional for correction of spinal trauma or conditions, such as curvature of the spine. Generally, an orthopedic stabilization system may include a pair of elongate members, such as spinal rods or plates, that are coupled to a bone or bones. For the sake of simplicity, the term "rod" is used throughout to refer to any elongate member. The rods are generally contoured and longitudinally disposed adjacent to vertebral bodies of a spine.

The strength and stability of the rod assembly can be increased by coupling the two rods with a cross-connector that extends substantially horizontal to the longitudinal axes of the rods across the spine. In some situations, the two rods are geometrically aligned such that the two rods are parallel to each other. However, the two rods are often not three dimensionally geometrically aligned in actual situations. There are several ways to address the variations of geometrical alignment. First, one or both of the rods can be bent to accommodate the transconnector. However, any bending in either of the rods can adversely affect the fixation to the spine and comprise clinical outcome. Furthermore, the bending can also adversely affect the mechanical properties of the rods. The transconnector can also be bent so that the disturbance to the rod positioning is minimized. As is the case with bending of the rods, the mechanical properties of the transconnector could be compromised.

Because of the forces acting along the transverse connector and the movement of the spinal rods, the connection between the transverse connector and the rod must be secure to avoid movement of the transverse connector along the spinal rod. Some rod fastening systems of transverse connectors use threaded fasteners to attach the transverse connector to adjacent rods. The threaded fastener can be a setscrew or a nut. Not tightening a threaded fastener enough may allow movement of the transverse connector. Overtightening a threaded fastener could result in damage to the system and failure of the transverse connector.

SUMMARY

Disclosed herein are methods and devices for interconnecting first and second longitudinal members extending along a spinal column of a patient. The devices are particularly suited for use in the cervical region of the spine.

In one aspect, there is disclosed a transconnector for connecting first and second spinal rods that are positioned longitudinally along a spine, comprising: a first cross member having a first clamp member adapted to clamp onto a first spinal rod, the first member having a first connecting region extending away from the clamp member; a second cross member having a second clamp member adapted to clamp onto a second spinal rod, the second member having a second connecting region extending away from the second clamp member toward the first member, wherein the second member and first member are interconnected along the first and second connecting regions; and a central attachment mechanism positioned at a location where the first and second members connecting member couple with one another, the central attachment mechanism configured to tighten and secure the first and second members relative to one another, wherein the central attachment mechanism includes a seat having a scalloped surface and a set screw having a scalloped surface that mates with the scalloped surface of the seat.

Other features and advantages should be apparent from the following description of various embodiments, which illustrate, by way of example, the principles of the described subject matter

DETAILED DESCRIPTION

Disclosed herein are methods and devices for interconnecting first and second longitudinal members extending along a spinal column of a patient. The devices are particularly suited for use in the cervical region of the spine.

FIGS. 1-5 illustrate various embodiments of exemplary transverse connectors, and in each of the illustrated embodiments the transverse connector generally includes a first connecting member and a second connecting member. Each pair of connecting member connect to each other transversely (i.e., across or substantially across the midline of the vertebral column) in a variety of configurations. Each pair of connecting members are fixed to each other by any of a variety mechanisms such as an attachment mechanism. Further, each embodiment of the transverse connector includes a clamping mechanism that is adapted to selectively lock a longitudinal member extending along a spinal column of a patient, such as a spinal fixation element, and in particular a spinal fixation rod. The fixation of the connecting member pairs and the clamping mechanisms allow for transverse as well as rotational adjustability of the transverse connectors.

A person skilled in the art will appreciate that while each transverse connector is described herein as being adapted to engage a spinal fixation element, and in particular a spinal fixation rod, that a transverse connector disclosed herein can be configured to engage a variety of spinal fixation devices, such as anchors, cables, fixation plates, etc. Moreover, the transverse connectors can include only one connector member for engaging a spinal fixation device, and the opposed terminal end of the transverse connectors can be adapted for other uses. For example, the opposed terminal end of the transverse connectors can be configured to be fixedly attached to a vertebra. The transverse connectors disclosed herein can also include any combination of features described and/or illustrated herein, and the transverse connectors are not limited to the illustrated embodiments.

As indicated above, the transverse connector in certain exemplary embodiments includes a first connecting member and a second connecting member that extend toward each other between each longitudinal member or spinal rod. The first and second connecting members can connect by a variety of mechanisms or configurations. The first and second connecting members can be generally elongate and positioned a distance apart from one another and adjusted transversely. The first and second connecting members can also be rotationally adjustable to allow the connecting members to be positioned as desired. The transverse and rotational adjustability of the transverse connectors allows them to mate to parallel, non-parallel, diverging, and converging spinal rods that are implanted within a patient's spinal system.

Figure 1:
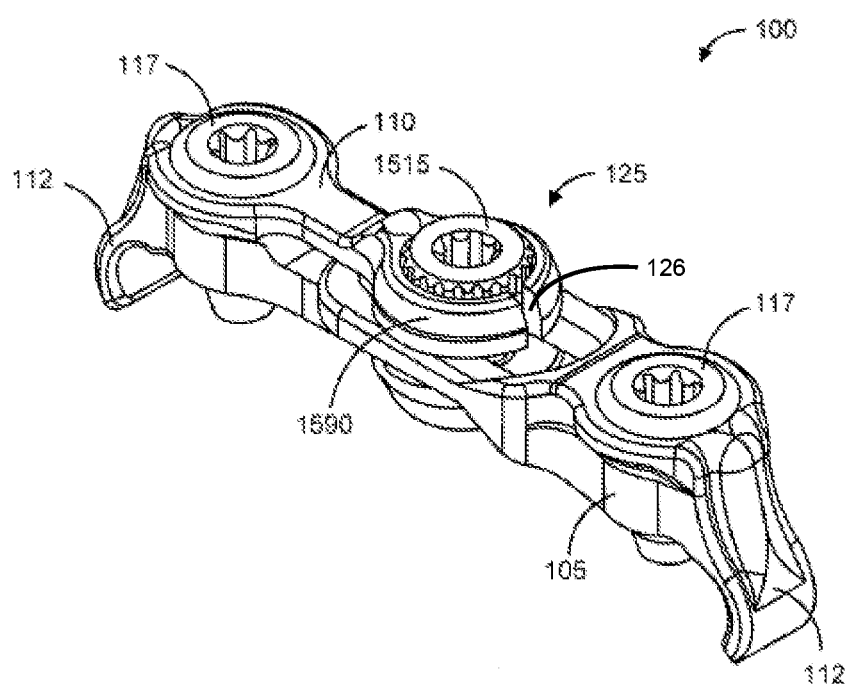
FIGS. 1 and 2 shows an exemplary transverse connector device 100 for interconnecting a pair of longitudinal members or rods connected to vertebrae of a spinal column.
Figure 2:
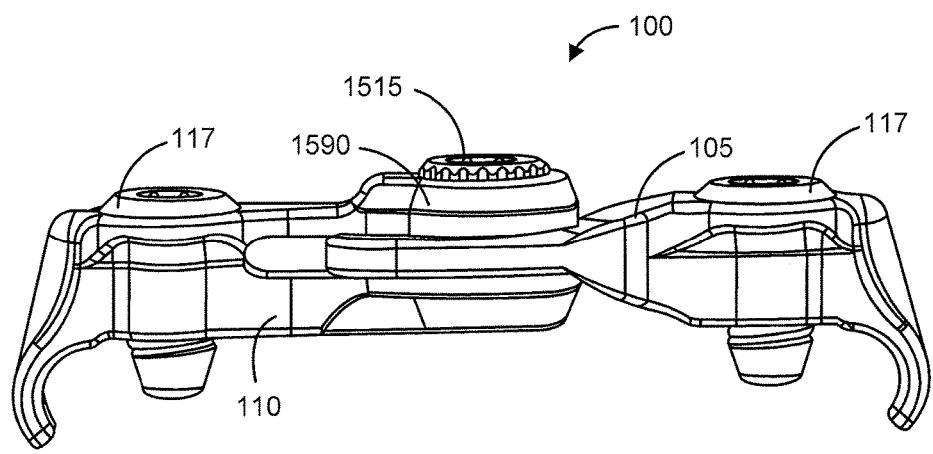

FIGS. 1 and 2 shows an exemplary transverse connector device 100 for interconnecting a pair of longitudinal members or rods connected to vertebrae of a spinal column. Although the transverse connector 100 is described herein as an interconnecting rod, it is contemplated that the transverse connector 100 may interconnect any suitable longitudinal member, such as plates or rods of other shapes, such as hexagonal rods.

With reference to FIGS. 1 and 2, the device includes a first member 105 that is rotatably and slidably connected to a second member 110. Each of the members has a hook portion 112 (or other type of attachment member) that is configured to couple to a spinal rod or other spinal connection device. The outer transverse end of each of the first and second members includes a fixation member, such as a screw 117, that can be used to secure each of the members to the spinal rod or a portion of the spine.

A central attachment mechanism 125 is positioned at a location where the first and second members interface with one another. The central attachment mechanism 125 can be used to tighten and secure the first and second members 105, 110 relative to one another. In this regard, the attachment mechanism 125 includes a compression nut 1515 that has a radially outward facing surface that is configured to mate with or engage with an inner surface of a seat in which it is mounted. In an embodiment, the mating outer and inner surfaces each have a scalloped profile. Thus, the radially outward facing surface of the compression nut 1515 is configured to engage a complementary shaped, radially inward facing contact surface of a seat 1590 to provide a locking mechanism that limits relative rotation between the seat 1590 and the nut 1550. In an embodiment, the seat 1590 and the nut 1515 form saw tooth-shaped or ribbed projections and the saw tooth or ribbed protrusions that interlock with one another. In some embodiments, a seat 1590 comprises a gap 126.

In some embodiments, the seat 1590 and the nut 1515 can provide a series of undulating or scalloped engaging members that are interlocked or provide an interference fit upon relative rotation of the nut. Accordingly, when the nut 1515 is received into the seat 1590, the radially outward facing surface of the compression nut 1515 engages the complementary shaped, radially inward facing contact surface of the seat. Thus, further relative rotation between the compression nut 1515 and the seat 1590 is prevented unless the seat 1590 deflects from, or bows out relative to the nut 1515.

In order for the nut 1515 to be removed from the seat 1590, the laterally opposed projections must be deflected to disengage the interlocking sawtooth arrangement between the sawtooth projections and the sawtooth protrusions. A tool can be used to facilitate deflection between the laterally opposed upwardly extending projections 1540 in order to release the compression nut 1515 from engagement with the coupling element 1505 so the coupling nut 1515 can be removed.

Figure 3:
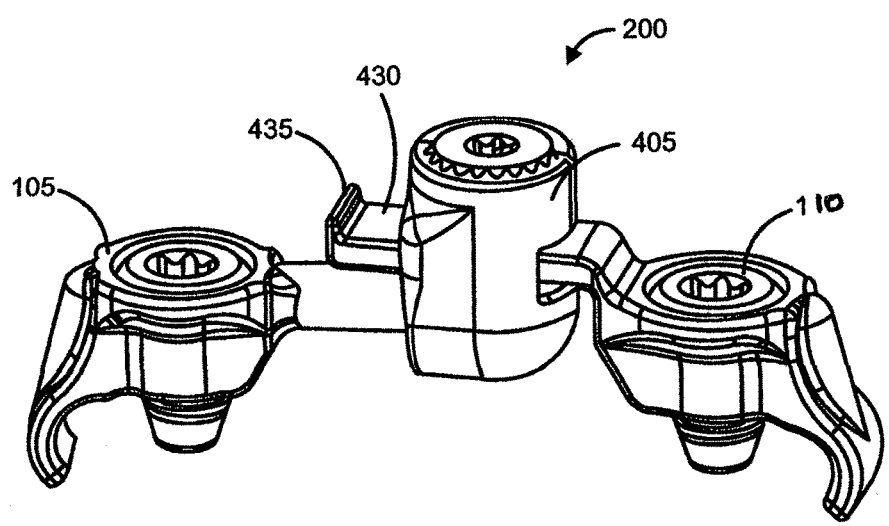
FIGS. 3-5 shows another embodiment of a cross-connector device.
Figure 4:
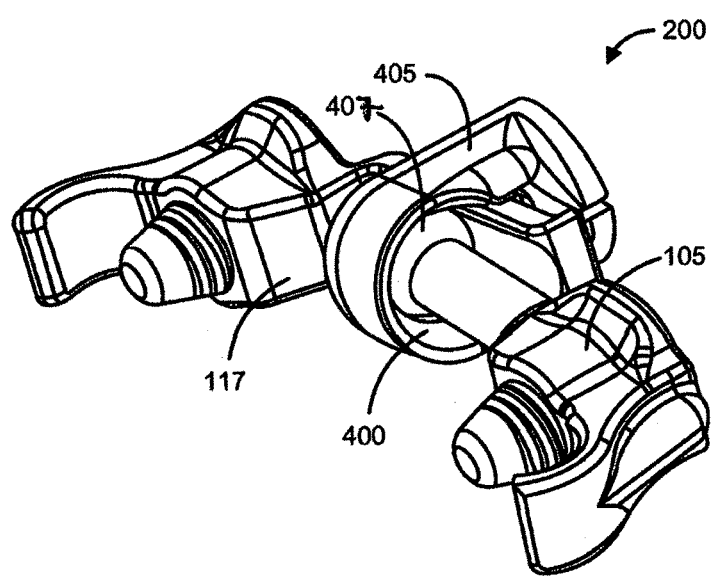
Figure 5:
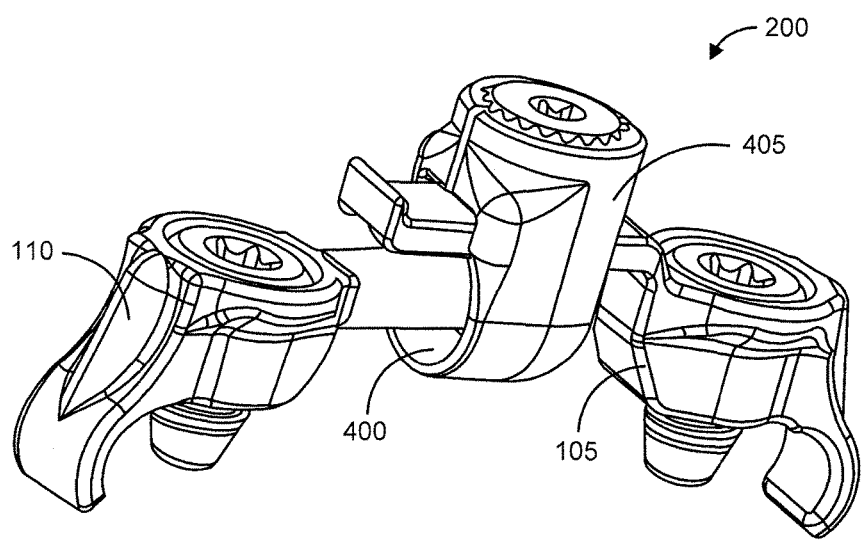

FIGS. 3-5 shows another embodiment of a cross-connector device 200. This embodiment includes a poly-axial range of movement between the first and second members 105, 110.

In this regard, as shown in FIG. 4, the first member 105 includes an elongated arm having a ball 407 located at its end. The ball fits into a complementary shaped, elongated socket 400 of a central member 405. The socket 400 is sized and shaped such that the ball can slide and rotate within the socket. This permits translational movement (along the length of the socket) and rotational movement of the first member relative to the second member. With reference to FIG. 3, the second member 110 also includes an elongated arm 430 that slidably fits through a slot in the central member 405. The end of the arm 430 has a stopper member 435 that limits the amount of translational movement of the arm through the socket.

In addition, the central member may include a locking element of the type described with respect to the device of FIGS. 1 and 2.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A transconnector for connecting first and second spinal rods that are positioned longitudinally along a spine, comprising:
   a first cross member having a first clamp member adapted to clamp onto a first spinal rod, the first cross member having a first connecting region extending away from the first clamp member;
   a second cross member having a second clamp member adapted to clamp onto a second spinal rod, the second cross member having a second connecting region extending away from the second clamp member toward the first cross member, wherein the second cross member and first cross member are interconnected along the first and second connecting regions;
   a central attachment mechanism positioned at a location where the first and second cross members couple with one another, the central attachment mechanism configured to tighten and secure the first and second cross members relative to one another, wherein the central attachment mechanism includes a seat having vertically extending ribs on an interior surface of the seat, and a set screw having vertically extending ribs that mate with the vertically extending ribs of the seat, wherein the seat has a noncontiguous round side surface, such that the seat partially surrounds the set screw, thereby providing a gap that extends through the side surface between the interior surface of the seat and the side surface of the seat, said gap providing an unobstructed passageway to the set screw when the transconnector is fully assembled.

2. A transconnector as in claim 1, wherein the ribs are saw tooth surfaces.

3. A transconnector as in claim 1, wherein the second cross member and first cross member are slidably interconnected along the first and second connecting regions.

4. A transconnector as in claim 1, wherein the second cross member and first cross member are rotatably interconnected along the first and second connecting regions.

5. A transconnector as in claim 1, wherein the central attachment mechanism includes a ball and socket.

6. A transconnector as in claim 1, wherein the gap of the seat forms a pair of surfaces of the seat that face one another.

\* \* \* \* \*